(12) United States Patent
Ceschini et al.

(10) Patent No.: US 8,378,676 B2
(45) Date of Patent: Feb. 19, 2013

(54) SYSTEM AND METHOD FOR DETECTING CORROSION PITTING IN GAS TURBINES

(75) Inventors: Giuseppe Fabio Ceschini, Florence (IT); Federico Iozzelli, Florence (IT)

(73) Assignee: Nuovo Pignone S.p.A., Florence (IT)

( * ) Notice: Subject to any disclaimer, the term of this patent is extended or adjusted under 35 U.S.C. 154(b) by 203 days.

(21) Appl. No.: 12/479,396

(22) Filed: Jun. 5, 2009

(65) Prior Publication Data

US 2010/0308818 A1    Dec. 9, 2010

(51) Int. Cl.
*G01V 3/00* (2006.01)
(52) U.S. Cl. ......................................... 324/300; 234/322
(58) Field of Classification Search .......... 324/300–322; 415/174.2, 170; 428/469, 472; 427/452, 427/453, 457; 416/241, 95; 29/889
See application file for complete search history.

(56) References Cited

U.S. PATENT DOCUMENTS

| | | | |
|---|---|---|---|
| 6,320,384 B1 * | 11/2001 | Doty et al. | 324/321 |
| 6,452,384 B1 | 9/2002 | Becker et al. | |
| 6,692,228 B2 * | 2/2004 | Turnquist et al. | 415/174.2 |
| 7,754,342 B2 * | 7/2010 | Hazel et al. | 428/632 |
| 8,157,504 B2 * | 4/2012 | Amaral et al. | 415/115 |
| 2003/0025497 A1 | 2/2003 | Collingwood et al. | |
| 2004/0051525 A1 | 3/2004 | Hatcher et al. | |
| 2007/0217672 A1 * | 9/2007 | Shannon et al. | 382/152 |
| 2009/0176110 A1 * | 7/2009 | Pabla et al. | 428/450 |

FOREIGN PATENT DOCUMENTS

| | | |
|---|---|---|
| EP | 0518635 A2 | 12/1992 |
| WO | WO 00/47986 A1 | 8/2000 |

OTHER PUBLICATIONS

International Search Report mailed Sep. 9, 2010 in counterpart international application No. PCT/EP2010/057852.
Written Opinion mailed Sep. 9, 2010 in counterpart international application No. PCT/EP2010/057852.

* cited by examiner

*Primary Examiner* — Brij B Shrivastav
(74) *Attorney, Agent, or Firm* — GE Global Patent Operation

(57) ABSTRACT

Methods and apparatuses for detecting corrosion in one or more blades of a gas turbine system includes a detection head having a shape that conforms to a surface geometry of a filet section of a gas turbine blade, whereby the detection head is operable to move along the axial length of the filet section for detecting corrosion pitting. At least one coil device located within the detection head induces a first magnetic field within an area of the filet in contact with the detection head. A receiver device is adapted to detect a signal corresponding to a second magnetic field received from the area of the filet exposed to the first magnetic field, where the second magnetic field is generated by induced currents in the area by the first magnetic field. A signal processing device then processes the detected signal for correlating a corresponding amplitude of the detected signal with the presence of corrosion pitting in the area such that the presence of corrosion pitting is determined without any casing disassembly of the gas turbine system.

24 Claims, 10 Drawing Sheets

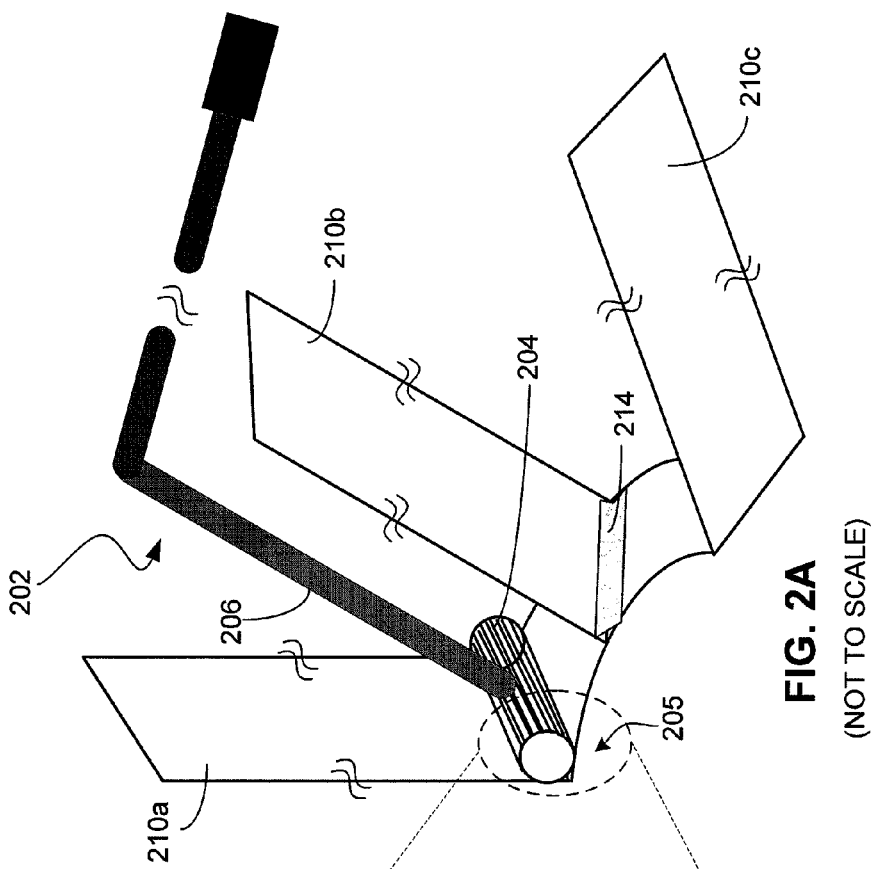
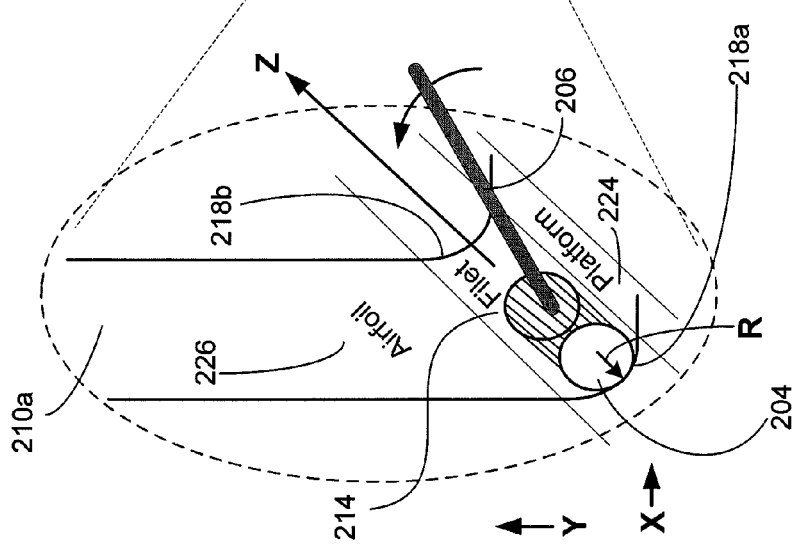

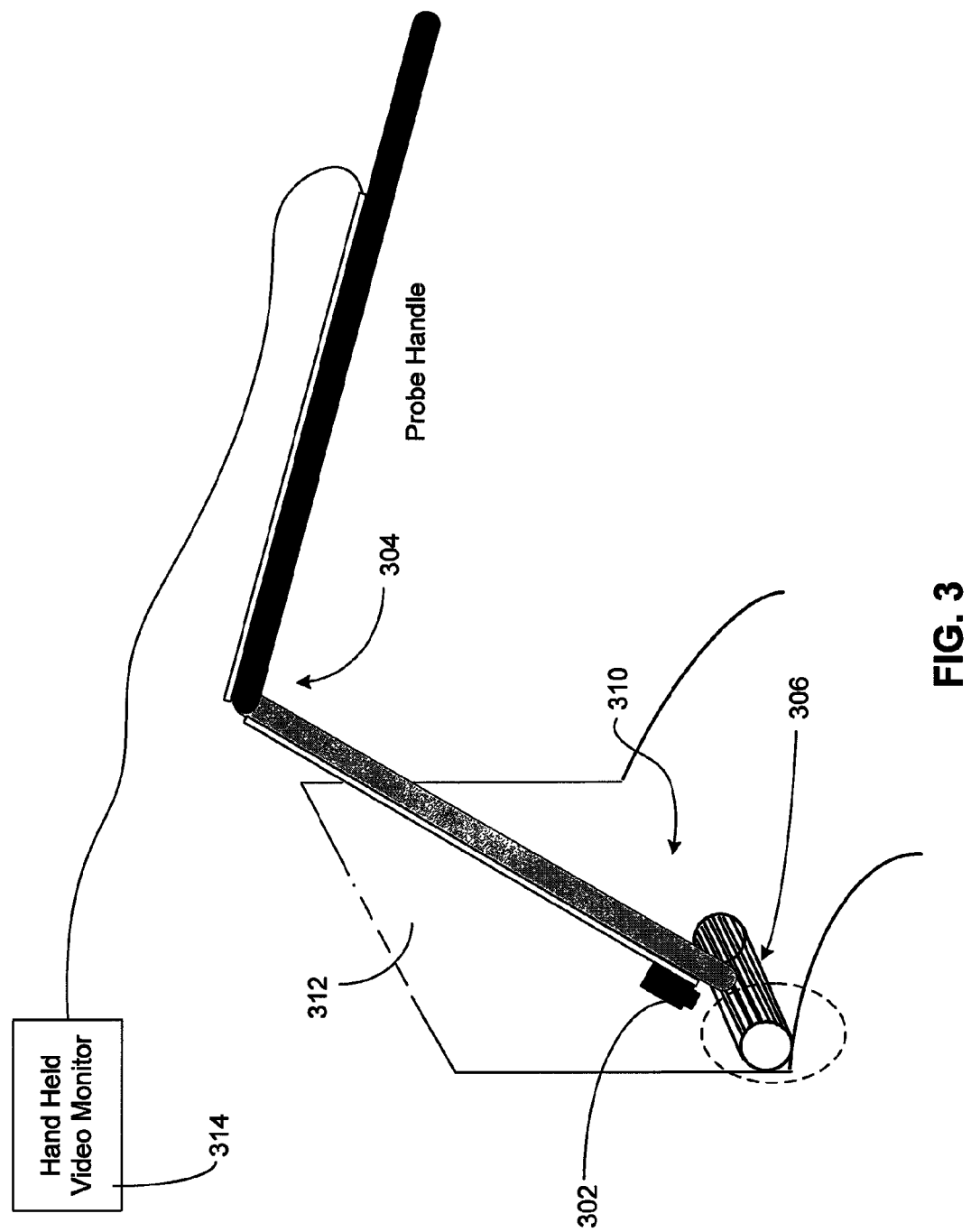

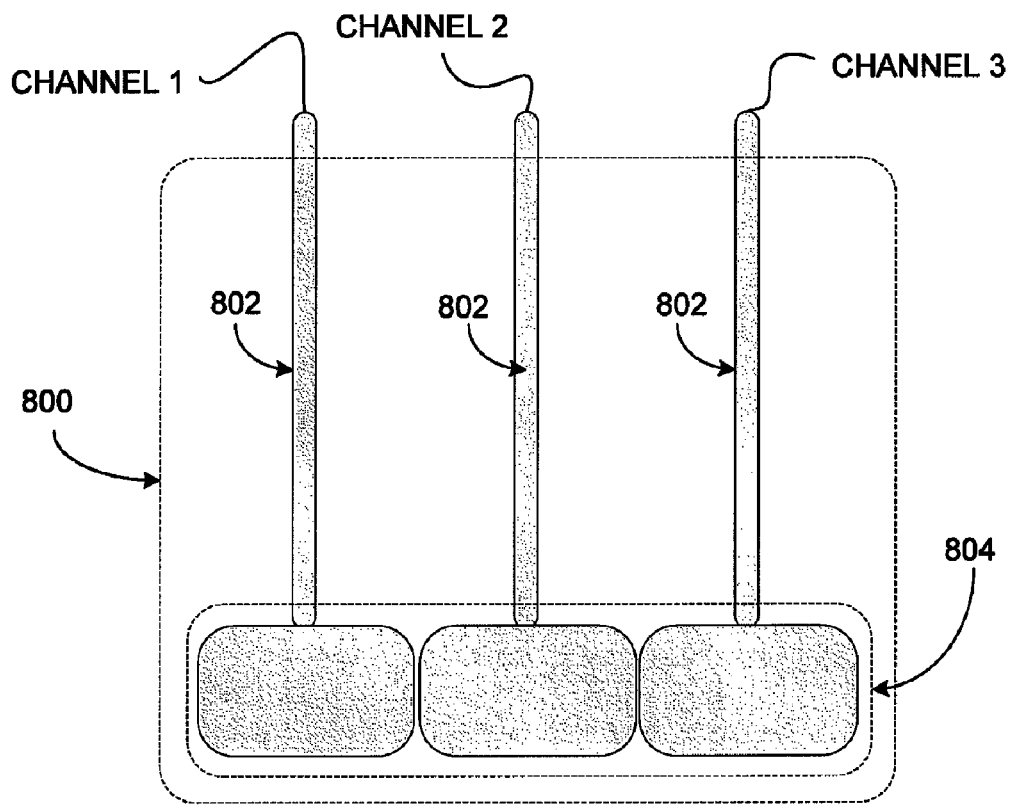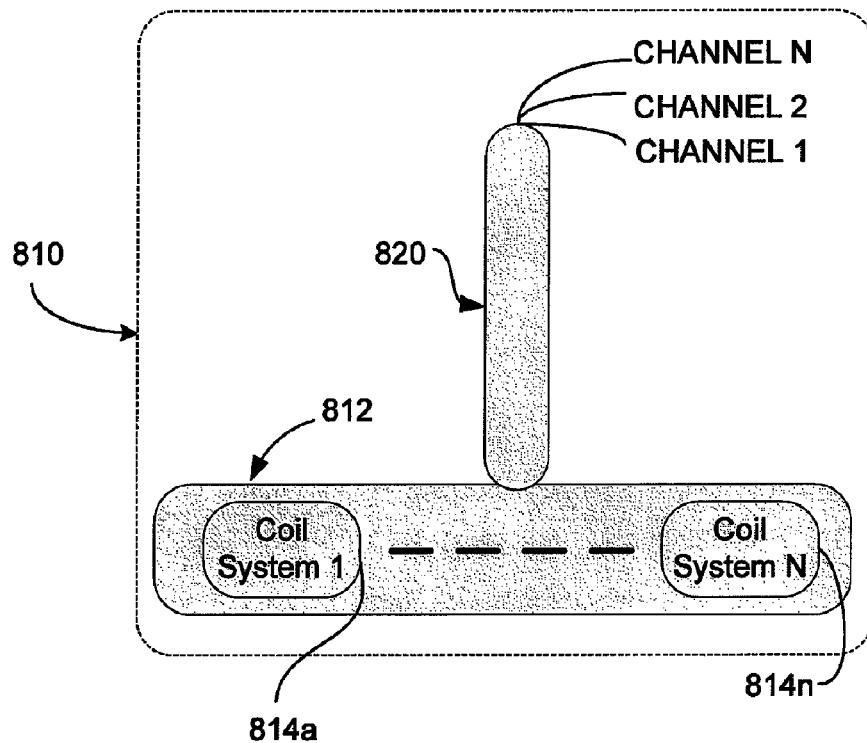
FIG. 8

US 8,378,676 B2

SYSTEM AND METHOD FOR DETECTING CORROSION PITTING IN GAS TURBINES

TECHNICAL FIELD

The present invention relates generally to the detection of corrosion in gas turbine systems, and, more particularly, to an apparatus and method for providing in-situ detection of corrosion pitting in gas turbine compressor blades.

BACKGROUND

As a fuel with low $CO_2$ emissions, natural gas has experienced a major expansion worldwide. When distance and topography between gas fields and consumer markets do not allow pipeline transport, the gas can be reduced to, for example, 1/600 of its free volume by liquefaction. Liquefied Natural Gas (LNG) plants liquefy purified natural gas in cryogenic heat exchangers so that the purified liquid natural gas can be stored in tanks prior to being loaded on designed tankers for transportation between an LNG plant and consumer regions. At the consumer regions, the LNG product is unloaded in an LNG receiving terminal, pumped up to pipeline pressure, and re-gasified for feeding into the buyer's natural gas pipeline grid.

In response to these increased demands, the size of LNG plants has, therefore, grown considerably over the past few decades. This, in turn, has contributed to lowering LNG production costs, while at the same time increasing the competitivity of the LNG marketplace. For example, in the 1980s, it was common practice to produce 2-3 million tons per steam per year. Present units produce 4-5 million tons per year, and engineering companies are now (i.e., 2009) planning plants with unit capacities in the order of 7-8 million tons per year.

In LNG plants, it is common practice to use, for example, gas turbines to drive the refrigerating compressors utilized in the cryogenic heat exchangers responsible for the liquefaction of natural gas. Thus, production output may be closely associated with reliable plant operation, in particular, gas turbine reliability. The reliable operation of gas turbine systems may be hampered by a myriad of different failure causes. As described in the following paragraphs, one such cause is the adverse effect of corrosion on the Inlet Guide Vanes (IGVs) and rotor blades of the gas turbine's turbo compressor.

LNG plants are typically located in marine coastal environments, where corrosive elements such as Chlorides and Sulphides are prevalent in the atmosphere. The Chlorides originate as a result of proximity to the sea, while the Sulphides are generated by the LNG plant's gas flares. The air filtration system of a gas turbine needs both correct design and maintenance, especially since it provides the key to the successful operation and reliability of the overall plant by purifying air that is inlet into the combustion section of the gas turbine system. Despite attempts to maintain reliable and effective air filtration, the presence of corrosive elements such as Chlorides and Sulphides in the various stages of the gas turbine system, such as, the axial compressor blades of the gas turbine (e.g., IGVs and R1 rotor blades) is unavoidable. These elements (i.e., Chlorides and Sulphides) may, for example, corrode the material construction of the gas turbine's IGVs and first stage (R1) rotor blades by causing corrosion pitting, which if undetected, eventually leads to the initiation and propagation of cracks within the blades. The consequences of such cracks are breakages in one or more of gas turbine's IGVs and R1 rotor blades, thus, causing an eventual gas turbine outage.

These outages are extremely costly. Usually, there is zero-redundancy associated with the production machinery/equipment of LNG plants. Within a given gas turbine train, the outage of one gas turbine can cause an overall train outage or, at least, a vast reduction of LNG production rate. As a consequence, LNG shipment may also be postponed, generating additional costs and/or profit losses that may be estimated in the range of $2-$7 Million Dollars/day depending on the specific plant size and production plan. For this reason all catastrophic failures, such as those generated by corrosion pitting, should be avoided since an outage of 7-10 days duration is the expected duration for restoring the system back to an operational status.

Thus, in order to avoid a gas turbine outage situation as a result of undetected failure conditions, it would be advantageous to provide in-situ corrosion detection within LNG gas turbine systems without the need for disassembling the gas turbine system (e.g., casing).

SUMMARY OF INVENTION

Various embodiments of the present invention provide methods and apparatuses for detecting corrosion pitting in turbine blades. In accordance with at least one embodiment, a corrosion detection device (e.g., EC probe device) for detecting corrosion in one or more blades of a gas turbine system comprises a detection head having a shape that conforms to a surface geometry of a filet section of a gas turbine blade, whereby the detection head is operable to move along the axial length of the filet section for detecting corrosion pitting. At least one coil device located within the detection head induces a first magnetic field within an area of the filet in contact with the detection head. A receiver device is adapted to detect a signal corresponding to a second magnetic field received from the area of the filet exposed to the first magnetic field, where the second magnetic field is generated by induced currents in the area by the first magnetic field. A signal processing device then processes the detected signal for correlating a corresponding amplitude of the detected signal with the presence of corrosion pitting in the area such that the presence of corrosion pitting is determined without any casing disassembly of the gas turbine system.

In accordance with one aspect, the at least one coil device comprises a plurality of coil devices located within the detection head and operable to each induce the first magnetic field within an area of the filet in contact with the detection head, whereby the detected signal includes a plurality of signals corresponding to the second magnetic field. The signal processing device is operable to process the plurality of detected signals for correlating corresponding amplitudes of the detected signals with the presence of corrosion pitting in the area, where each of the processed plurality of detected signals corresponds to a signal channel associated with a respective one of the plurality of coil devices, thereby providing for multi-channel detection of corrosion pitting.

In accordance with another aspect, the at least one coil device comprises separate coils including: (a) a first coil operable to generate the first magnetic field; and (b) at least one other coil operable to receive the second magnetic field.

According to one aspect, the receiver device may include: (a) a first and a second coil device operable to generate a first and a second received signal from the second magnetic field, respectively; (b) a first and a second band-pass filter device respectively coupled to the first and the second coil device, wherein the first and the second band-pass filter device are operable to filter the first and the second received signal, respectively; and (c) differential amplifier device coupled to the first and the second band-pass filter device, wherein the differential amplifier is operable to differentially amplify the filtered first and the filtered second received signal and generate the detected signal.

According to another aspect, the detection head may include a substantially cylindrical shape including a radius that corresponds to a curvature radius of the filet, or a substantially cylindrical shape including a radius that is less than the curvature radius corresponding to the filet.

According to another aspect, the detection apparatus further includes a handle section coupled to the detection head, the handle section including a flexible portion operable to move the detection head into a measurement position by enabling contact between the detection head and the filet section of the one of a plurality of first stage R1 rotor blades based on manipulating the flexible portion and detection head between the plurality of inlet guide vanes located at the front of the R1 rotor blades.

According to another aspect, the detection apparatus further includes a video camera coupled to the handle section, the video camera located in proximity to the detection head and operable to assist an operator move the detection head into the measurement position.

According to another aspect, the detection apparatus further includes a driver device operable to generate a drive signal that is applied to the at least one coil device, whereby the driver device manipulates at least one characteristic (e.g., amplitude, frequency, etc.) of the drive signal for producing a signal-to-noise ratio associated with the detected signal that exceeds a designated threshold.

According to another aspect, the signal processing device includes a digital signal processing (DSP) device comprising: (a) an analog-to-digital convertor operable to digitize the detected signal amplitude; (b) a first storage region operable to store an amplitude corresponding to the detected signal with other stored detected signal amplitudes based on the amplitude corresponding to the detected signal and the other stored detected signal amplitudes corresponding to a detected corrosion pit; (c) a second storage region operable to store reference data associated with a plurality of pre-generated corrosion pitting areas created on a sample filet surface of a gas turbine blade; and (d) a processor section operable to compare the amplitude corresponding to the detected signal with the stored reference data for determining the presence of corrosion pitting in the filet section.

According to another aspect, the first storage region includes time-stamp information that is added to both the amplitude corresponding to detected signal and the other stored detected signal amplitudes for calculating a time interval between the determinations of corrosion pitting in the filet section. The first storage region may also include drive signal information that is added to the stored detected signal amplitude and the other stored detected signal amplitudes.

In accordance with another embodiment, a probe device for detecting corrosion in one or more blades of a gas turbine system includes: (a) a detection head having a shape that conforms to a surface geometry of a filet section of a gas turbine blade, the detection head operable to move along the filet section for detecting corrosion pitting; (b) at least one transducer device located within the detection head and operable to induce a first magnetic field within an area of the filet in contact with the detection head; (c) a receiver device operable to detect a signal corresponding to a second magnetic field received from the area of the filet exposed to the first magnetic field, wherein the second magnetic field is generated by induced currents in the area by the first magnetic field; and (d) a signal processing device operable to process the detected signal for correlating a corresponding amplitude of the detected signal with the presence of corrosion pitting in the area, whereby the presence of corrosion pitting is determined without any casing disassembly of the gas turbine system.

In accordance with yet another embodiment, a probe device for detecting corrosion in one or more blades of a gas turbine system includes: (a) a detection head having a shape that conforms to a surface geometry of a filet section of a gas turbine blade, the detection head operable to move along the filet section for detecting corrosion pitting; (b) a transceiver device located within the detection head and operable to induce a first magnetic field within an area of the filet in contact with the detection head and detect a signal corresponding to a second magnetic field received from the area of the filet exposed to the first magnetic field, wherein the second magnetic field is generated by induced currents in the area by the first magnetic field; and (c) a signal processing device operable to process the detected signal for correlating a corresponding amplitude of the detected signal with the presence of corrosion pitting in the area, whereby the presence of corrosion pitting is determined without any casing disassembly of the gas turbine system.

According to one aspect, the transceiver device may include: (a) a transmitter operable to generate the first magnetic field; and (b) a receiver operable to receive the second magnetic field and generate the detected signal amplitude. The transmitter may include a first coil device, and a coil driver operable to apply an electrical drive signal to the first coil device. The receiver may include a second coil device; a third coil device; and a differential amplifier coupled to the second and the third coil device and operable to differentially amplify a second and a third signal received from the second and the third coil device, respectively, whereby the differential amplifier generates the detected signal.

In accordance with at least one other embodiment, a method of detecting corrosion in one or more blades of a gas turbine system is provided. The method comprises detecting corrosion pitting along the axial length of a filet section of a gas turbine blade by conforming the detecting to the surface geometry of the filet section, and inducing a first magnetic field within an area of the filet during the detecting of the corrosion. A signal corresponding to a second magnetic field received from the area of the filet exposed to the induced first magnetic field is detected, where the second magnetic field is generated by induced currents in the area by the induced first magnetic field. The detected signal is then processed by correlating a corresponding amplitude of the detected signal with the presence of corrosion pitting in the area. The presence of corrosion pitting is thus determined without any casing disassembly of the gas turbine system.

In accordance with at least one aspect, conforming the detecting to the surface geometry comprises using a probe head having a cylindrical shape that includes a radius that is substantially the same as or less than a radius of curvature associated with the filet section.

In accordance with at least one other embodiment, a corrosion pitting detection unit comprises a plurality of probe devices, where each probe device includes: (a) a detection head having a shape that conforms to a surface geometry of a filet section of a gas turbine blade, the detection head operable to move along the axial length of the filet section for detecting corrosion pitting; (b) at least one coil device located within the detection head and operable to induce a first magnetic field within an area of the filet in contact with the detection head; (c) a receiver device operable to detect a signal corresponding to a second magnetic field received from the area of the filet exposed to the first magnetic field, wherein the second magnetic field is generated by induced currents in the area by the first magnetic field; and (d) a signal processing device operable to process the detected signal for correlating a corresponding amplitude of the detected signal with the presence of corrosion pitting in the area, where the presence of corrosion pitting is determined without any casing disassembly of the gas turbine system, and whereby the results of the detected signal processed by each signal processing device of the plurality of probe devices is output on a corresponding channel.

It will be appreciated by those skilled in the art that the foregoing brief description and the following detailed description are exemplary and explanatory of the present invention, but are not intended to be restrictive thereof or limiting of the advantages which can be achieved by this invention. Additionally, it is understood that the foregoing summary of the invention is representative of some embodiments of the invention, and is neither representative nor inclusive of all subject matter and embodiments within the scope of the present invention. Thus, the accompanying drawings, referred to herein and constituting a part hereof, illustrate embodiments of this invention, and, together with the detailed description, serve to explain principles of this invention.

BRIEF DESCRIPTION OF THE DRAWINGS

Aspects, features, and advantages of embodiments of the invention, both as to structure and operation, will be understood and will become more readily apparent when the invention is considered in the light of the following description made in conjunction with the accompanying drawings, in which like reference numerals designate the same or similar parts throughout the various figures, and wherein:

FIGS. 2A-2C illustrate the mechanical construction and relative positioning of the EC probe device relative a gas turbine system rotor blade under inspection in accordance with an embodiment of the present invention;

FIG. 3 illustrates an imaging device used in cooperation with the EC probe device in accordance with an embodiment of the present invention;

FIG. 8 illustrates an example of a unit incorporating a multi-channel EC probe device in accordance with an embodiment of the present invention.

DESCRIPTION OF EMBODIMENTS OF THE INVENTION

The following describes various embodiments and aspects of the present invention that utilizes Eddy Currents (EC) for the detection and analysis of the corrosive characteristics (e.g., corrosion pitting) found in gas turbine rotor blades. Accordingly, a novel EC detection probe and application methodology is provided for detecting corrosion pitting in the first stages of gas turbine rotor blades. The first stages of the gas turbine rotor blades (i.e., R1 rotor blades) are typically more susceptible to corrosion pitting. Moreover, using the probe device, the first stage rotor blades (i.e., R1) are directly accessible by a user via an opening in the intake plenum of the gas turbine.

The corrosively generated pits ("a corrosion pit") may or may not be substantially circular and generally include indentations in a material's surface. These indentations, although very small (i.e., typically having depths and diameters of less than 1 millimeter), lead to more serious defects such as cracks. In the case of the first stages (i.e., R1) of a gas turbine's rotor blades, detection of corrosion pitting avoids the subsequent initiation and propagation of cracks, whereby the creation of such cracks can lead to rotor blade breakages during the operations of a gas turbine and thus leading to a catastrophic failure. While cracks provide a sharp discontinuity that makes them suitable for conventional detection via signal phase changes using EC detection equipment, a corrosion pit does not exhibit such a sharp discontinuity. Therefore, according to at least one embodiment of the present invention, sensitive receiver designs may be utilized for the detection of signal amplitude changes resulting from the presence of a corrosion pit.

Figure 1A:
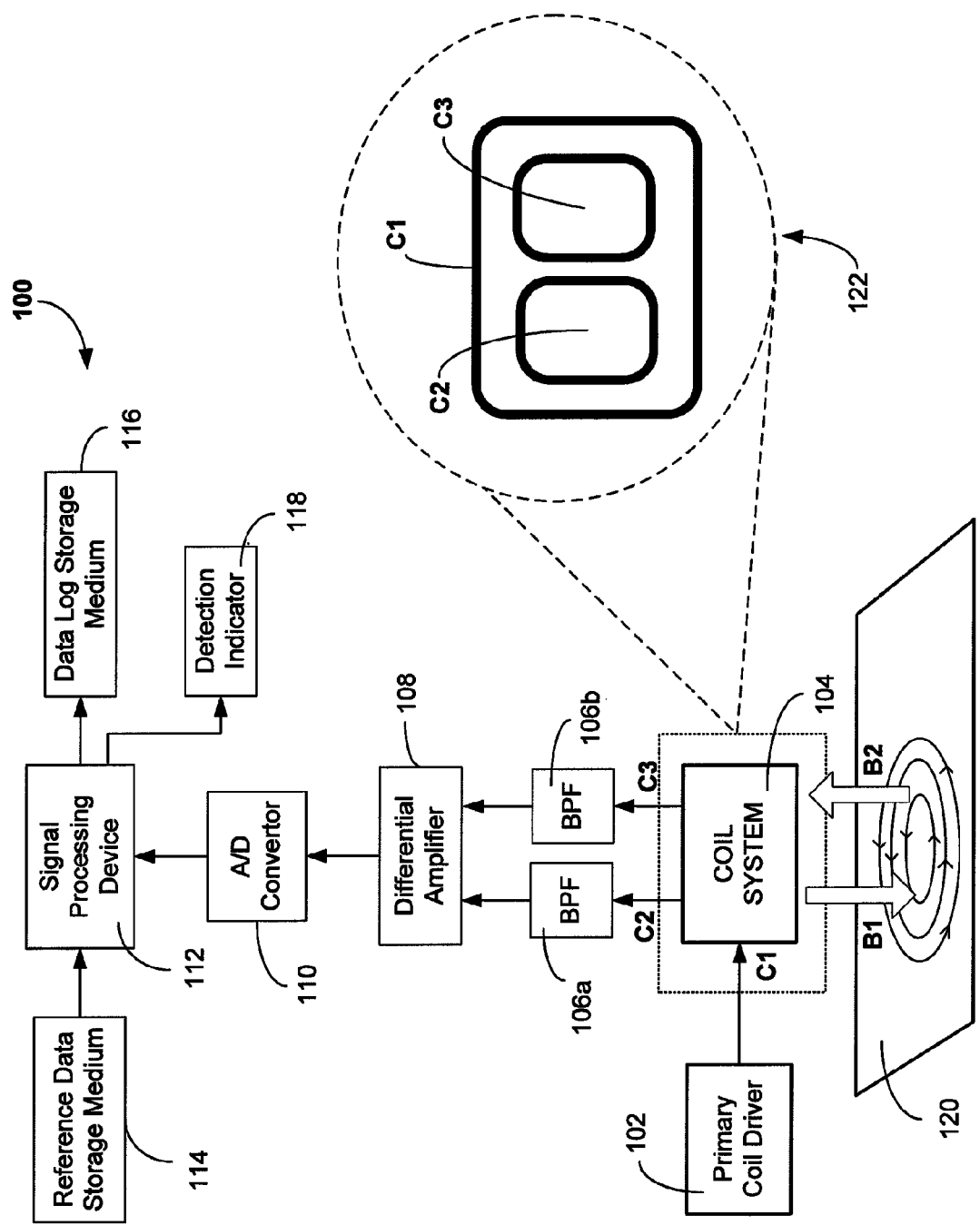
FIG. 1A illustrates a block diagram of an Eddy Current (EC) probe device in accordance with an embodiment of the present invention.

FIG. 1A schematically depicts an EC probe device 100 in accordance with an embodiment of the present invention. Device 100 comprises a primary coil driver 102, a coil system 104, band-pass (BP) filters 106a and 106b, a differential amplifier 108, an analog-to-digital (A/D) convertor 110, a signal processing device 112, a reference data storage medium 114, a data log storage medium 116, and a detection indicator 118 (e.g., a visual display, audio buzzer). The operation of the EC probe device 100 is further explained in relation to the flow diagrams illustrated in FIG. 5 and FIG. 6.

The primary coil driver 102 includes an electrical signal source that provides an alternating drive signal (e.g., sinusoidal signal, pulsed signal, ramped signal, etc.) to the coil system 104 for inducing eddy currents in the surface 120 of the material under inspection (i.e., filet portion of gas turbine R1 rotor blades). Coil system 104 may include three coil devices, as illustrated in the expanded bottom view 122. As depicted at 122, coil C1 is a primary coil device operable to generate a primary magnetic field (B1) that is induced in surface 120, which produces eddy currents within the surface 122. Coil devices C2 and C3 are measurement coils used to receive a net magnetic field comprised of the interaction between the generated primary magnetic field (B1) and the generated eddy current magnetic field (B2) from surface 122. As previously mentioned, sensitive receiver designs may be utilized for the detection of signal amplitude changes resulting from the presence of a corrosion pit. One such design consideration applies to the measurement coils (i.e., C2, C3). These coils should exhibit a coil diameter that has a comparable geometry (e.g., diameter) to that of the indentations caused by corrosion pitting. For example, a coil diameter of 1.6 mm may be used to detect corrosion pits having diameters of 0.25 mm, 0.50 mm, and 0.75 mm, and a depth of 0.25 mm, 0.50 mm, and 0.75 mm, respectively.

Measurement coil devices C2 and C3 are each coupled to the inputs of BP filters 106a and 106b, respectively. The BP filters 106a, 106b serve to reduce or eliminate, among other unwanted artifacts, signals such as high frequency noise and low frequency signal variations that may occur as a result of physically manipulating the EC probe device 100 relative to measurement area when, for example, the device is utilized as a hand-held device. In addition, BP filters 106a and 106b also enhance the signal-to-noise (S/N) ratio of the signals received by coil devices C2 and C3, respectively. The configuration of coils C1, C2, and C3 illustrated at 122 is one example of many different kinds of possible coil arrangements. For example, another configuration may include positioning measurement coils C2 and C3 on either side of drive coil C1 (located in the center). According to another example, a single coil such as coil C1 may be utilized to both generate the primary magnetic field (B1) and receive a net magnetic field (B2) generated as a result of eddy currents induced by the primary magnetic field (B1).

The output from BP filters 106a and 106b are coupled to the differential inputs of differential amplifier 108. When no defects are present on surface 122, the filtered inputs received from the BP filters 106a, 106b at the differential inputs of the differential amplifier 108 are substantially the same. Consequently, the differential amplifier 108 generates an output voltage of low signal amplitude close to zero. Alternatively, if defects are present on surface 122, the filtered inputs received from the BP filters 106a, 106b at the differential inputs of the differential amplifier 108 are not the same. Consequently, the differential amplifier 108 generates an increased output voltage. As one of the measurement coils (i.e., C2 or C3) moves over a pitted area (due to corrosion), the reactive component of this coil (e.g., C2) changes relative to the other coil (e.g., C3). This in turns causes a differential change in signal current that is applied to the differential amplifier 108 and, thus, an increase in output voltage.

The amplitude of the generated output signal may depend on several factors such as, but not limited to, the geometry of the pit (e.g., 0.3×0.45 millimeters), the sensitivity of the measurement coils to changes in eddy-current-induced magnetic fields caused by the pit, and the optimization of the electrical drive parameters associated with the coil driver 102 (e.g., waveform, amplitude, and frequency of the signal driving the primary coil). The generated output signal may be converted from an analog to a digital format by A/D convertor 110 prior to being processed at the signal processing device 112. Alternatively, the analog to a digital conversion may be performed within the signal processing device 112 without the need for a separate device such as A/D convertor 110.

The signal processing device 112 provides various processing on the digitized amplitude signals output from the differential amplifier 108. For example, the signal processing device 112 may perform threshold detection in order to determine whether the detected amplitude constitutes an amplitude signal caused by the detection of a corrosion pit. Signal processing device 112 also accesses reference data from the reference data storage medium 114 in order to correlate the received amplitude signal with existing reference data (e.g., various digitized amplitude values) entered in the reference data storage medium 114. Each reference data entry found within reference data storage medium 114 may optionally provide information associated with a corrosion pit having a specific geometry and/or dimension. Alternatively, the accessed reference data may confirm the presence or absence of a corrosion pit based on the degree of amplitude correlation between a received amplitude signal (i.e., digitized) and various amplitude values (i.e., digitized) entered in the reference data storage medium 114 without providing geometry and/or dimension information. Additional digital signal processing (DSP) such as digital filtering and equalization may also be carried out on the received amplitude signals in order to further aid the detection of corrosion pits.

The detection indicator 118 alerts a user of the probe device 100 once it has been determined that a corrosion pit has been detected. The detection indicator 118 may comprise a visual indicator such as a light emitting device (e.g., LED) and/or an audio indicator such as a buzzer.

The signal log storage medium 116 stores data information associated with each detected corrosion pit. Once the signal processing device 112 confirms the detection of a corrosion pit, it stores the detected amplitude value along with time-stamp information within the signal log storage medium 116. The time-stamp may comprise date (e.g., year/month/day) and time (e.g., 24 hour clock) information associated with each detected corrosion pit, which may, among other uses, provide a means for calculating the different time intervals between the different occurrences of detecting corrosion pitting in the gas turbine rotor blades. The signal log storage medium 116 may also store drive signal information corresponding to each of the detected amplitude values and time-stamp information. The stored drive signal information may include the amplitude characteristics, shape, and frequency of the signal applied to primary coil C1 based on the detection of a corrosion pit.

Although FIG. 1A illustrates a separate reference data storage medium 114 and signal log storage medium 116, both storage mediums (i.e., 114 and 116) may be integrated within the signal processing device 112.

Figure 1B:
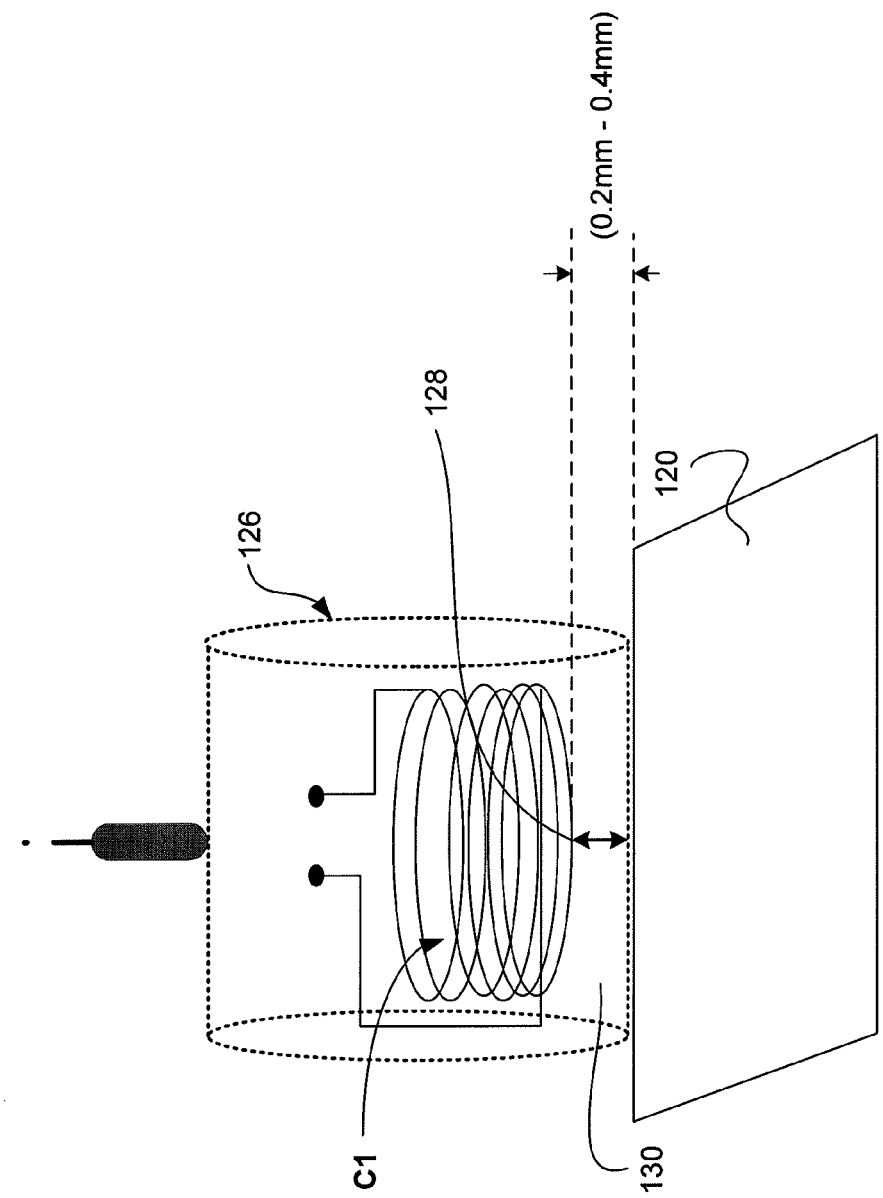
FIG. 1B illustrates the position of the EC probe head relative to surface under inspection in accordance with an embodiment of the present invention.

FIG. 1B illustrates the position of an EC probe detection head 126 relative to surface 120 under inspection in accordance with an embodiment of the present invention. As shown, the primary coil device C1, along with measurement coils C2 and C3 (not shown in FIG. 1B), is located within the probe detection head 126. In operation, the probe head detection 126 is contactively applied to the surface 120 under inspection (e.g., an R1 rotor blade). The distance between Coil C1 and surface 120 is called lift-off, which affects the mutual inductance of the coils. In the example shown in FIG. 1B, the lift-off may be in the range of 0.2-0.4 millimeters (mm). The distance between coil end 128 and surface 120 may be about 0.2 mm. In addition, outer-surface 130 of probe detection head 126 may comprise an additional protective layer (not shown) having a thickness of about 0.2 mm (e.g., 0.2 mm of PTFE adhesive tape).

Figure 2C:
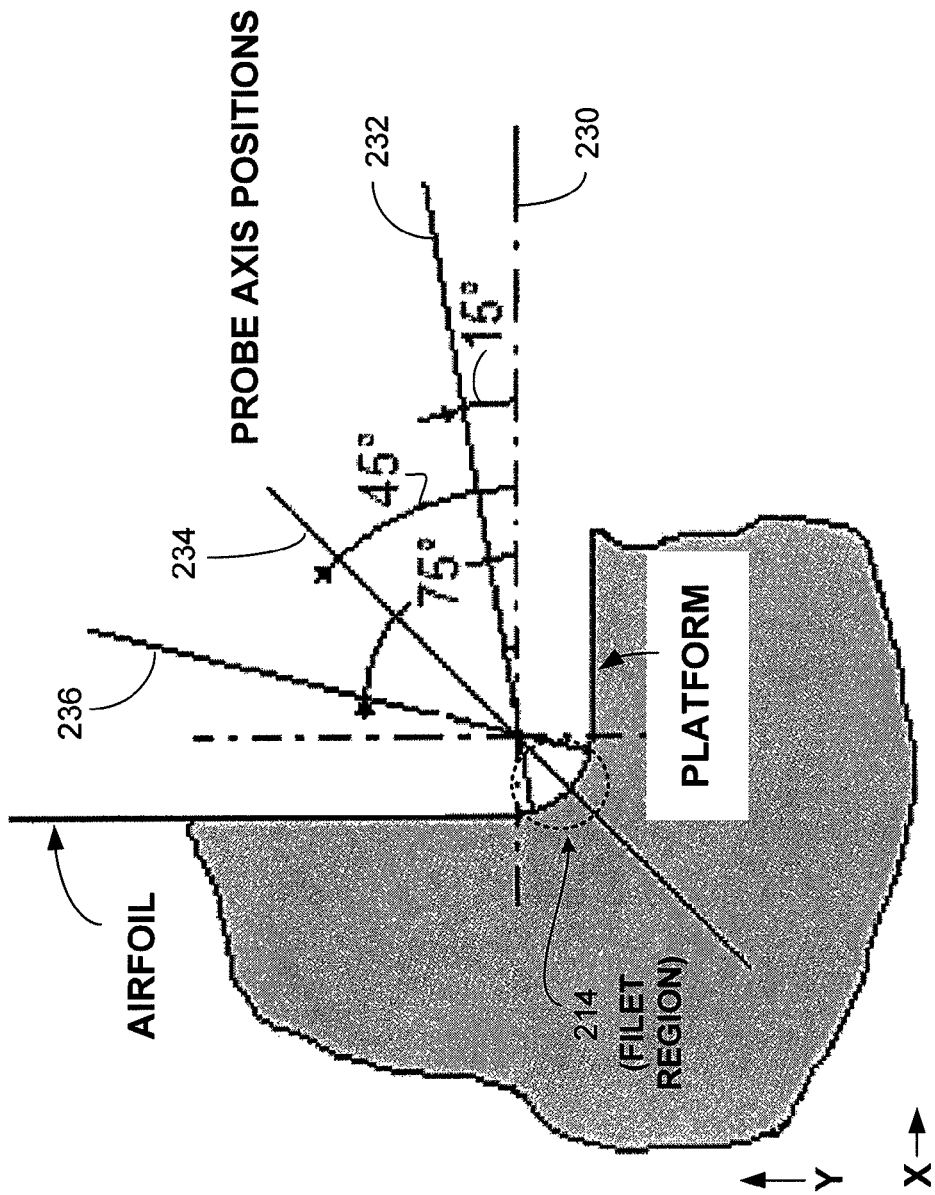

FIGS. 2A-2C illustrate the mechanical construction and relative positioning of an EC probe device 202 relative a gas turbine system rotor blade under inspection in accordance with an embodiment of the present invention. As shown in FIG. 2A, the EC probe device 202 comprises a probe detection head 204, a probe stem 206, and a probe guide 208 or extended handle. In FIG. 2A, the size of the probe device 202 relative to rotor blades 210a, 210b, and 210c is exaggerated for aiding the illustrative process. For example, the length of the probe head 204 relative to the length of the filet section 214 of each of the rotor blades is around ⅙. The length of the probe guide 208 may be in the region of 30 centimeters (cm), while the probe stem may have a length of about 5 cm.

The axis of the probe guide 208 may be substantially perpendicular to the axis of the probe stem 206, whereby the probe guide 208 facilitates the manipulation of the probe device 202 into measurement position such that physical contact is established between the probe head 204 and the filet section 214 of rotor blade 210a. This is also illustrated with the aid of the expanded view of region 205 shown in FIG. 2B.

As shown in FIG. 2B, the filet region 214 of rotor blade 210a is a region located between platform 224 and airfoil 226. The filet region of the rotor blades are of particular interest in detecting corrosion pitting according to the described embodiments of the present invention. During corrosion pitting detection, the probe head 204 is manipulated to contactively slide along the length of the filet 214 between filet edge 218a and 218b in the Z direction. During this sliding motion, the angle between the axis of the probe stem 206 and horizontal plane is kept relatively constant. The probe head 204 is manipulated to contactively slide along the length of the filet 214 multiple times. Each time, the probe stem 206 is rotated in the XY plane in order to form a new angle between the axis of the probe stem 206 and the horizontal plane. By changing the angle, the primary coil device C1 induces a primary magnetic field (B1) in a different area of the filet 214. By contactively sliding the probe head 204 along the length of the filet 214 at different angles, corrosion detection measurements covering the entire filet region is facilitated.

This angular variation in the probe stem 206 is illustrated in the cross sectional view of the rotor blade 210a depicted in FIG. 2C. According to the example shown in FIG. 2C, during the corrosion detection measurements, the probe stem is rotated in the XY plane to form three angles between the axis of the probe stem 206 and horizontal plane 230. More specifically, firstly, the probe head 204 is manipulated to contactively slide along the length of the filet 214 at an angle of 15 degrees, as defined by 232. Second, the probe head 204 is manipulated to contactively slide along the length of the filet 214 a second time at an angle of 45 degrees, as defined by 234. Finally, the probe head 204 is manipulated to contactively slide along the length of the filet 214 at an angle of 75 degrees for a third and final time, as defined by 236.

The number or slides and angles utilized during detection measurements can be varied. However, once a corrosion pit is detected, the probe head 204 is manipulated to contact that particular corrosion affected area. Once in the corrosion affected area, the angle between the axis of the probe stem 206 and horizontal plane 230 can be varied to determine whether other corrosion pits are also present in that particular section of the filet 214.

FIG. 3 illustrates an imaging device 302 used in cooperation with an EC probe device 304 in accordance with an embodiment of the present invention. The imaging device 302 (e.g., video camera) may be located in proximity to the probe device's 304 probe detection head 306 for the purpose of providing the user of the device 304 with an enhanced visual view of the filet portion 310 of the rotor blade 312 under inspection. The captured images may be displayed to the user on a handheld or portable video monitor 314.

Figure 4:
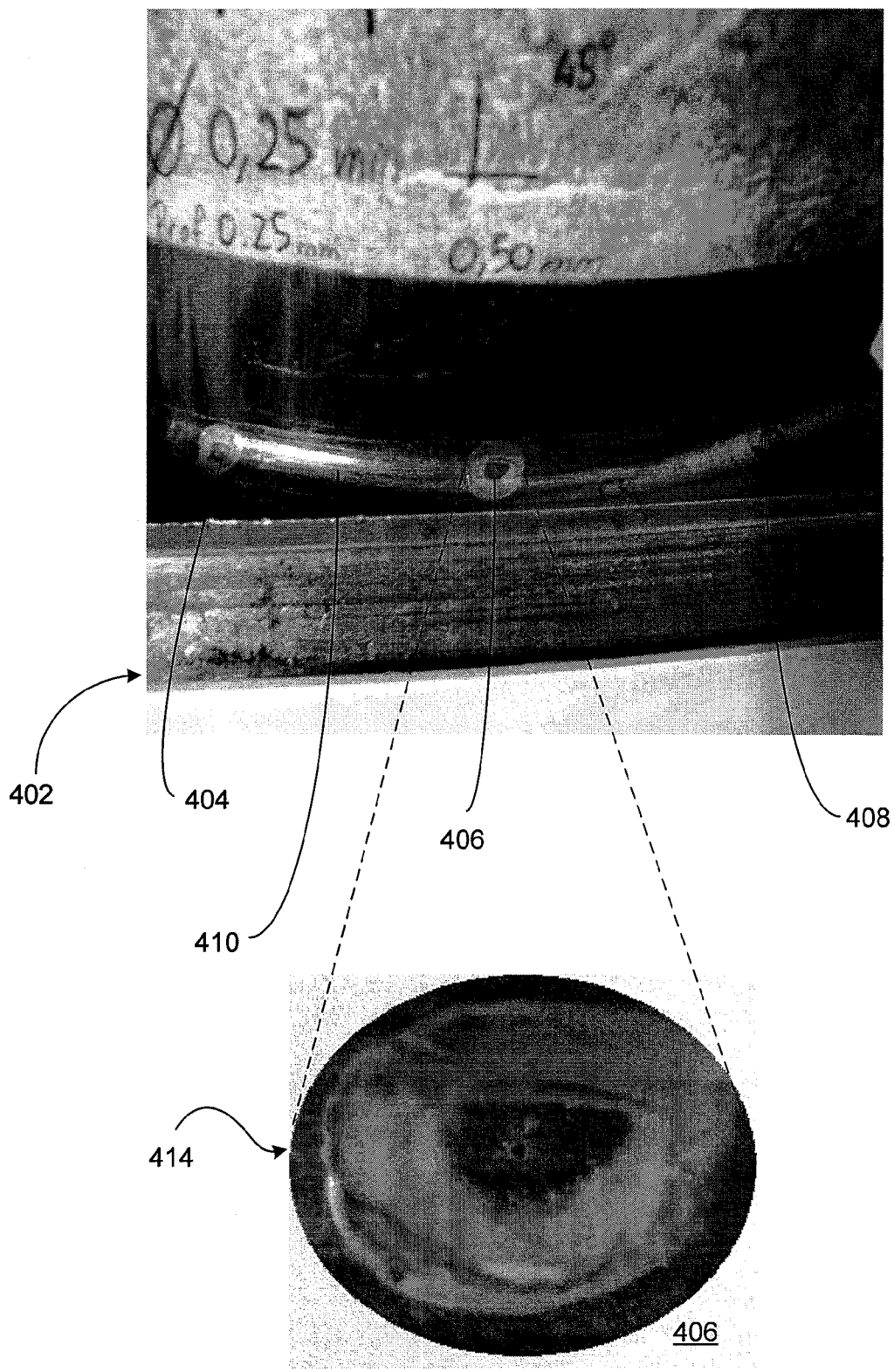
FIG. 4 illustrates a photographic image of a calibration block 402 used in the generation of stored reference data according to an embodiment of the present invention.

FIG. 4 illustrates a photographic image of a calibration block 402 used in the generation of the reference data that is stored in the reference data storage medium 114 (FIG. 1) according to an embodiment of the present invention. The calibration block comprises a plurality of pre-generated corrosion pitting areas 404, 406, 408 that are created on a sample filet surface 310 using electrical discharge machining (EDM). The illustrated example shows several pre-generated corrosion pitting areas 404, 406, 408 each having different diameters and depths that have been accurately formed on the sample filet surface 310 using EDM. Pre-generated corrosion pit area 404 includes a diameter of 0.25 mm and a depth of 0.25 mm. Pre-generated corrosion pit area 406 includes a diameter of 0.50 mm and a depth of 0.50 mm. Also, pre-generated corrosion pit area 408 includes a diameter of 0.75 mm and a depth of 0.75 mm. As defined at 414, an expanded view of pre-generated corrosion pit 406 is provided.

When an EC probe device such as device 100 (FIG. 1) performs a corrosion pit measure on the pre-generated corrosion pitting areas 404, 406, 408, each measurement will generate a specific signal amplitude that corresponds to each of pre-generated corrosion pitting areas 404, 406, 408. Therefore, each amplitude correlates with a particular corrosion pit having a know geometry. These signal amplitudes and their corresponding geometries may form at least some of the reference data that is stored. In this manner signal amplitudes that are generated during field tests can be correlated with the reference data in order to determine the existence of corrosion pitting. Optionally, the approximate geometry of any detected corrosion pit may also be provided.

Figure 5:
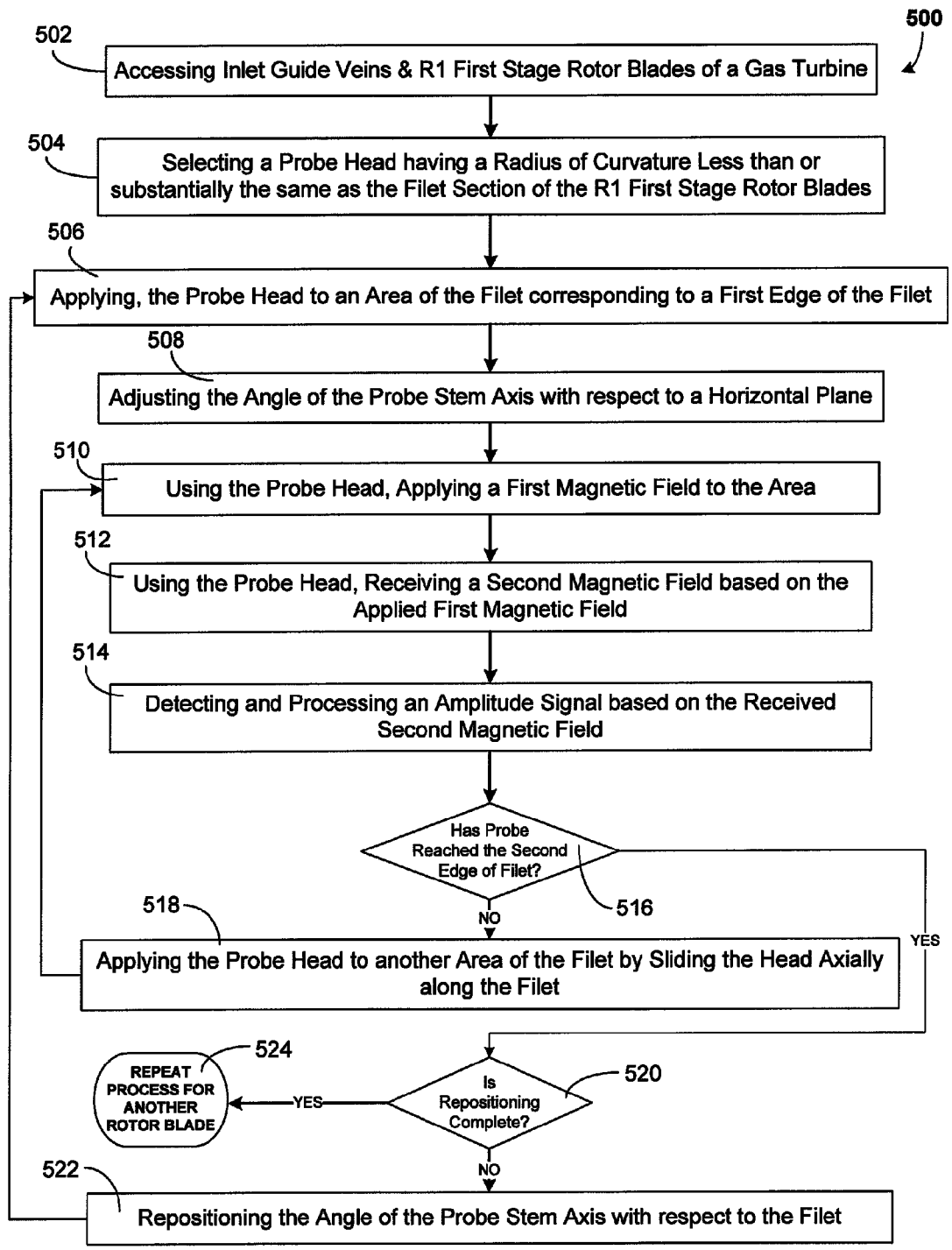
FIG. 5 illustrates an operation flow diagram Of the EC probe device according to an embodiment of the present invention.

FIG. 5 illustrates an operational flow diagram 500 associated with EC probe device 100 (FIG. 1) according to an embodiment of the present invention. Flow diagram 500 is described with the aid of FIGS. 1 and 2. At step, 502, a user accesses the inlet guide veins (IGVs) and the R1 rotor blades located directly behind the IGVs using an opening in the intake plenum at the front of the compressor mouth (i.e., bell mouth) of a gas turbine.

At step 504, a probe detection head having a radius of curvature less than or substantially the same as the filet section of the R1 rotor blades under inspection is selected. For example, radius R (FIG. 2B) of the probe detection head 204 (FIG. 2B) is designed to be slightly less than the radius of curvature of the filet section 214 (FIG. 2B).

At step 506, the probe head 204 is applied to the first edge 218a (FIG. 2B) of the filet 214. At step 508, the angle between the probe stem 206 (FIG. 2B) and the horizontal plane 230 (FIG. 2C) is then set at a relatively constant value of around, for example, 15 degrees, as defined at 232 (FIG. 2C).

At step 510, the drive coil C1 (FIG. 1A) within the probe head 204 applies a primary magnetic field to the area corresponding to the first edge 218a (FIG. 2B) of the filet 214. Using the measurement coils C2, C3 (FIG. 1A) within the probe head 204, a second magnetic field is detected based on the current induced in the conductive surface of the first edge 218a (FIG. 2B) area of the filet 214 (step 512). Based on the received second magnetic field by coils C2 and C3, an amplitude signal may be generated and processed by the differential amplifier 108 (FIG. 1A) and the signal processing device 112 (FIG. 1A) on the basis of a detected corrosion pit (step 514).

At step 516, it is determined whether the probe head 204 has reached the second edge 218b (FIG. 2B) area of the filet 214. If (YES) the probe head 204 has reached the second edge 218b (FIG. 2B) area (step 516), it is determined whether the repositioning of the probe angle between the probe stem 206 (FIG. 2B) axis and the horizontal plane 230 (FIG. 2C) has been completed (step 520). For example, if the probe head 204 is operated using three angles of 15, 45, and 75 degrees, the repositioning is completed if measurements are carried out for all three angles of 15, 45, and 75 degrees. If (YES) repositioning is completed (step 520), the process of operational flow diagram 500 is repeated for another R1 rotor blade (step 524).

If (NO) repositioning is not complete (step 520), the probe angle between the probe stem 206 (FIG. 2B) axis and the horizontal plane 230 (FIG. 2C) is changed to the next desired angle (step 522). For example, if the probe head 204 is operated using three angles of 15, 45, and 75 degrees, and the current angle is 15 degrees, the probe is then manipulated to the next angular setting to form a 45 degree angle. Following step 522, process steps 506, 508, 510, 512, 514, and 516 are then repeated.

If (NO) at step 516, the probe head 204 has not reached the second edge 218b (FIG. 2B) area, the probe head 204 is applied to another section of the filet 214 by sliding along the Z axis (FIG. 2B) direction of the filet 214 (step 518). Following step 518, process steps 510, 512, 514, and 516 are repeated.

Figure 6:
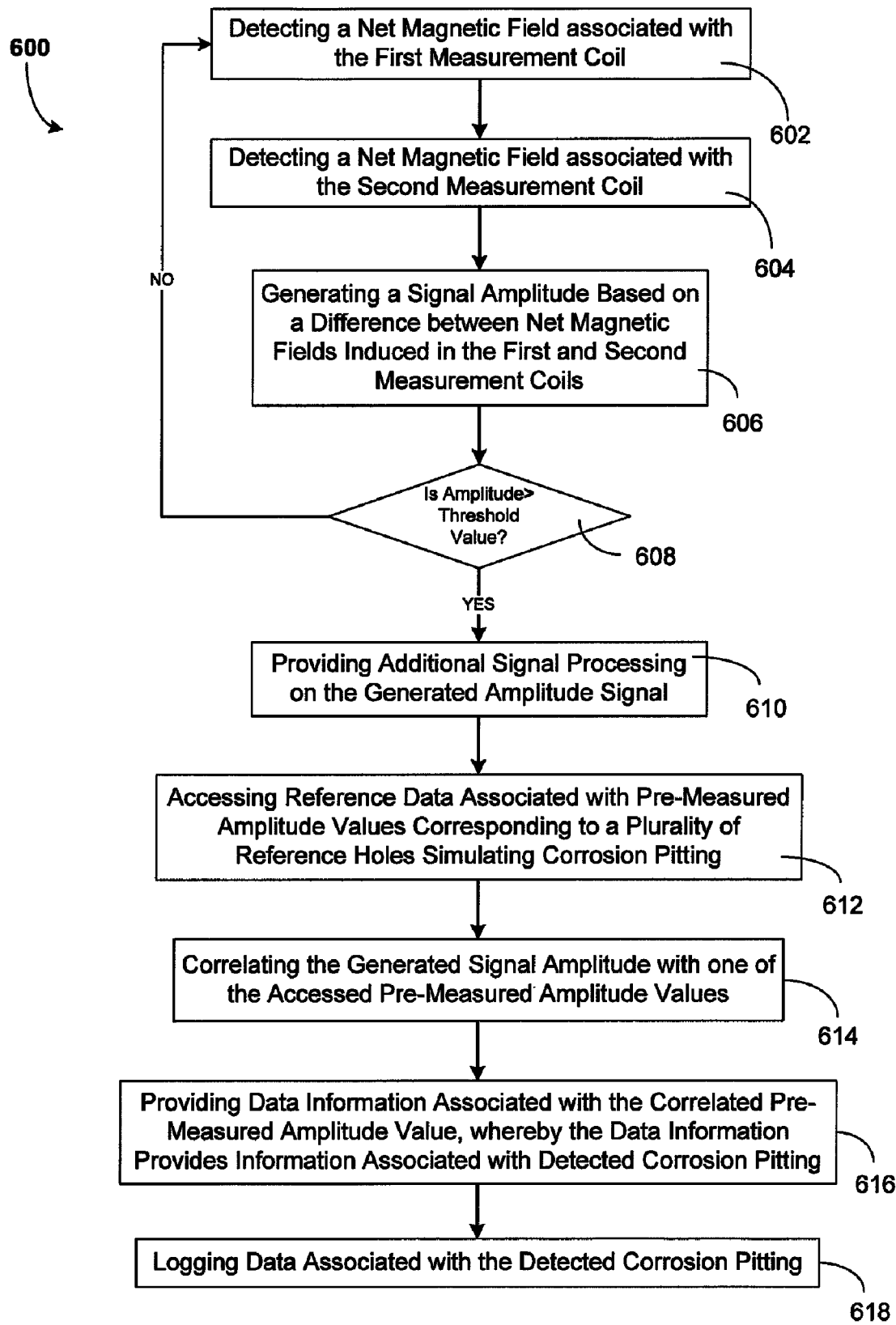
FIG. 6 illustrates an operation flow diagram of the signal processing performed by the EC probe device according to an embodiment of the present invention.

FIG. 6 shows an operation flow diagram 600 for the signal processing performed by the EC probe device 100 (FIG. 1A) in detecting a corrosion pit according to an embodiment of the present invention. At step 602, a net magnetic field is detected by measurement coil C2 (FIG. 1A). Similarly, at step 604, a net magnetic field is also detected by measurement coil C3 (FIG. 1A). The net magnetic field is a function of the interaction between the primary magnetic field generated by coil C1 (FIG. 1A) and the magnetic field generated by the eddy-currents induced in the conductive surface of the filet 214 (FIG. 1B).

At step 606, the differential amplifier 108 (FIG. 1A) generates a signal amplitude when a different net magnetic field is experienced between measurement coils C2 and C3. For example, if measurement coils C2 and C3 are receiving a net magnetic field from the surface of the filet 214 having no corrosion pits, the current magnitude induced in both measurement coils will be substantially the same. Thus, the differential amplifier 108 will not generate a signal exhibiting an increase in amplitude. However, if measurement coil C2 receives a net magnetic field from an area of the filet 214 where there is a corrosion pit, the corrosion pit will disrupt the flow of eddy-currents in that area such that the net magnetic field detected by coil C2 changes relative to the net magnetic field detected by coil C3. Under these conditions, the differential amplifier 108 will generate a signal exhibiting an increase in amplitude.

At step 608, it determined whether the signal generated by the differential amplifier 108 exceeds a predetermined threshold value. This threshold detection is carried out within signal processing device 112. If (NO) the signal generated by the differential amplifier 108 fails to exceed the predetermined threshold value, process steps 602, 604, and 606 are repeated. If (YES) the signal generated by the differential amplifier 108 exceeds the predetermined threshold value (step 608), additional signal processing (e.g., digital filtering, equalization, etc.) may be carried out within signal processing device 112 (Step 610).

At step 612, the signal processing device 112 accesses the reference data storage medium 114 in order to utilize the stored reference data. As previously described, the stored reference data may include premeasured amplitude values that correspond to various pre-generated corrosion pits. Using the accessed reference data, the signal processing device 112 correlates the detected amplitude signal generated by the differential amplifier 108 with one of the premeasured amplitude values of the accessed reference data (step 614).

Based on the correlated premeasured amplitude value, data information (e.g., corrosion pit geometry) associated with the detected corrosion pit may also be accessed from the reference data storage medium 114 using the signal processing device 112 (step 616). Data information (e.g., time-stamp data, pit geometry data, etc.) associated with the detected corrosion pit may then be logged by the signal processing device 112 in the data log storage medium 116 (step 618).

Figure 7:
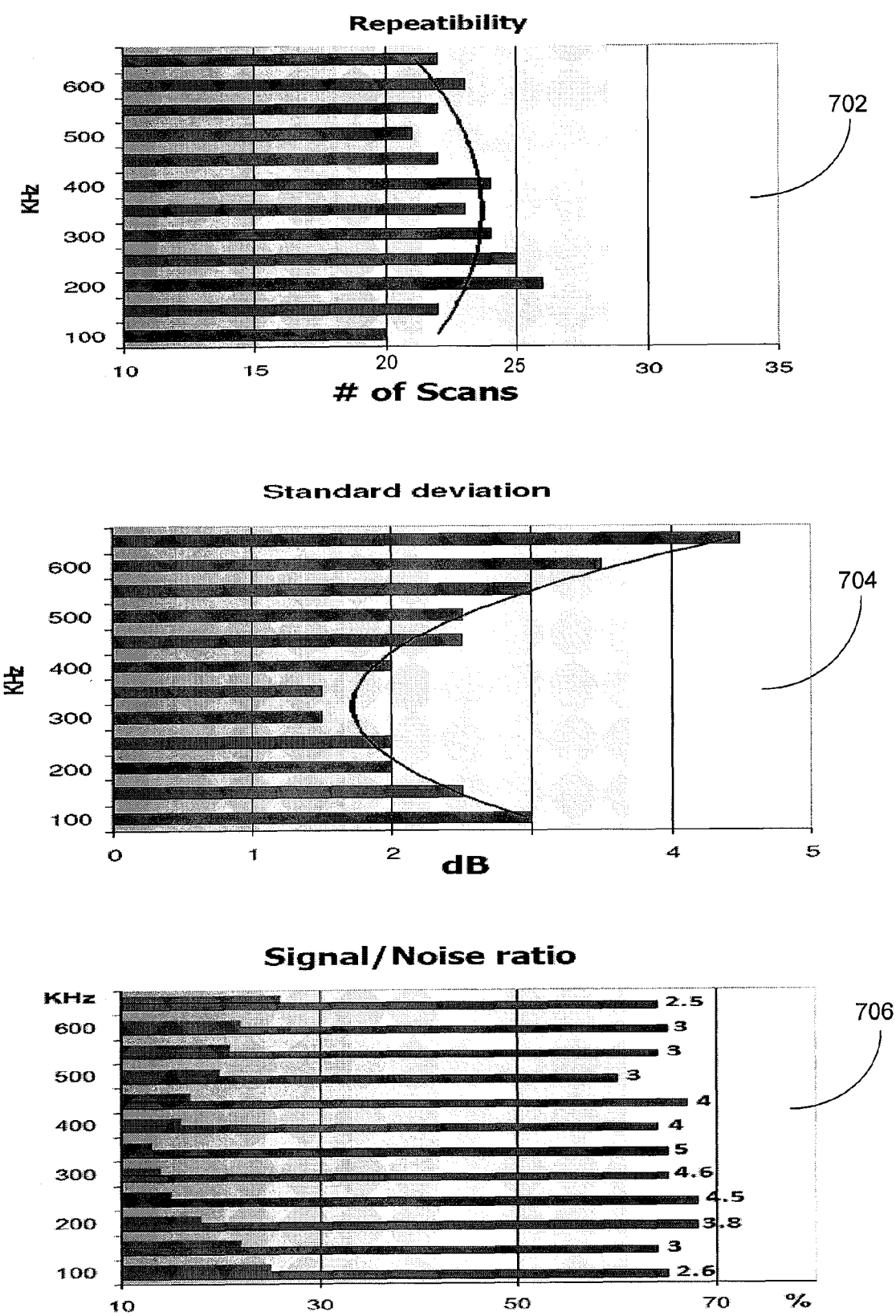
FIG. 7 illustrates experimental performance data associated with determining the operating parameters of the EC probe device according to an embodiment of the present invention.

FIG. 7 illustrates experimental performance data associated with determining the operating parameters of an EC probe device such as EC probe device 100 (FIG. 1A) according to an embodiment of the present invention. Graph 702 shows the repeatability of measurements carried out by an EC probe operated over a frequency range of 100-600 KHz. The frequency range applies to frequencies used to drive the primary coil of the EC probe under evaluation. As shown, frequencies in the range of 300-400 KHz desirably provide relatively the same measurement repeatability (e.g., detected amplitude values).

Graph 704 shows a measure of standard deviation associated with the detected signal amplitudes over a frequency range of 100-600 KHz. As shown, frequencies in the range of 300-400 KHz also provide a relatively constant standard deviation for the amplitude values detected by the EC probe.

Graph 706 shows a measure of signal-to-noise (S/N) ratio associated with the detected signal amplitudes over a frequency range of 100-600 KHz. As shown, in relation to the amplitude values detected by the EC probe, frequencies in the range of 300-400 KHz also exhibit the highest S/N ratios. Therefore, using such experimental evaluations, a suitable range of operating frequencies (e.g., 300-400 KHz) may be determined for a particular EC probe device.

It may be possible to incorporate several EC probe devices into a single unit in order to conduct measurements over an increased surface area of a filet section. In such a configuration, a multi-channel EC probe device may be provided, where each channel accesses measurement data. For example, a three channel device may be utilized. Such examples are shown in FIG. 8. According to one embodiment, a multi-channel probe device 800 may include three discrete probe devices 802 that are configured such that their respective probe detection heads are coupled to each other to form a longitudinally enlarged probe head 804. Each discrete probe device 802 constitutes a single channel and may, for example, comprise the same design as EC probe device 100 (FIG. 1A). According to another embodiment, a multi-channel EC probe 810 may comprise a single probe head 812 incorporating multiple coil systems 814a-814n, whereby each coil system may, for example, include the same configuration as coil system 104 (FIG. 1A). The stem 820 of multi-channel EC probe 810 may house a signal multiplexer (not shown) that sequentially reads received signals from each coil system 814a-814n. The processing of the received signals may be carried out using either an individual processing device (e.g., device 112, FIG. 1A) or a parallel processing approach incorporating multiple processing devices (e.g., multiple devices 112, FIG. 1A). It will be appreciated that a myriad of different processing architectures may be employed in the accessing and processing of multiple channels.

The present invention has been illustrated and described with respect to specific embodiments thereof, which embodiments are merely illustrative of the principles of the invention and are not intended to be exclusive or otherwise limiting embodiments. Accordingly, although the above description of illustrative embodiments of the present invention, as well as various illustrative modifications and features thereof, provides many specificities, these enabling details should not be construed as limiting the scope of the invention, and it will be readily understood by those persons skilled in the art that the present invention is susceptible to many modifications, adaptations, variations, omissions, additions, and equivalent implementations without departing from this scope and without diminishing its attendant advantages. For instance, except to the extent necessary or inherent in the processes themselves, no particular order to steps or stages of methods or processes described in this disclosure, including the figures, is implied. In many cases the order of process steps may be varied, and various illustrative steps may be combined, altered, or omitted, without changing the purpose, effect or import of the methods described. It is further noted that the terms and expressions have been used as terms of description and not terms of limitation. There is no intention to use the terms or expressions to exclude any equivalents of features shown and described or portions thereof. Additionally, the present invention may be practiced without necessarily providing one or more of the advantages described herein or otherwise understood in view of the disclosure and/or that may be realized in some embodiments thereof. It is therefore intended that the present invention is not limited to the disclosed embodiments but should be defined in accordance with the claims that follow.

What is claimed is:

1. A probe device for detecting corrosion in one or more blades of a gas turbine system, the device comprising:
   (a) a detection head having a shape that conforms to a surface geometry of a filet section of a gas turbine blade, the detection head operable to move along the axial length of the filet section for detecting corrosion pitting;
   (b) at least one coil device located within the detection head and operable to induce a first magnetic field within an area of the filet in contact with the detection head;
   (c) a receiver device operable to detect a signal corresponding to a second magnetic field received from the area of the filet exposed to the first magnetic field, wherein the second magnetic field is generated by induced currents in the area by the first magnetic field; and
   (d) a signal processing device operable to process the detected signal for correlating a corresponding amplitude of the detected signal with the presence of corrosion pitting in the area,
   wherein the presence of corrosion pitting is determined without any casing disassembly of the gas turbine system; and
   wherein the receiver device comprises:
   (i) a first and a second coil device operable to generate a first and a second received signal from the second magnetic field, respectively;
   (ii) a first and a second band-pass filter device respectively coupled to the first and the second coil device, wherein the first and the second band-pass filter device are operable to filter the first and the second received signal, respectively; and
   (iii) a differential amplifier device coupled to the first and the second band-pass filter device, wherein the differential amplifier is operable to differentially amplify the filtered first and the filtered second received signal and generate the detected signal.

2. The device according to claim 1, wherein the at least one coil device comprises separate coils including:
   (a) a first coil operable to generate the first magnetic field; and
   (b) at least one other coil operable to receive the second magnetic field.

3. The device according to claim 1, wherein the detection head comprises a substantially cylindrical shape including a radius that corresponds to a curvature radius of the filet.

4. The device according to claim 1, wherein the detection head comprises a substantially cylindrical shape including a radius that is less than or substantially equal to a curvature radius corresponding to the filet.

5. The device according to claim 1, wherein the gas turbine blade comprises one of a plurality of first stage R1 rotary blades located behind a plurality of inlet guide vanes.

6. The device according to claim 1, wherein the induced currents comprise Eddy Currents.

7. The device according to claim 1, further comprising a driver device operable to generate a drive signal that is applied to the at least one coil device, wherein the driver device manipulates at least one characteristic of the drive signal for producing a signal-to-noise ratio associated with the detected signal that exceeds a designated threshold.

8. The device according to claim 7, wherein the at least one characteristic comprises drive signal amplitude.

9. The device according to claim 7, wherein the at least one characteristic comprises drive signal frequency.

10. The device according to claim 7, wherein the at least one characteristic comprises a combination of drive signal amplitude and drive signal frequency.

11. A probe device for detecting corrosion in one or more blades of a gas turbine system, the device comprising:
   (a) a detection head having a shape that conforms to a surface geometry of a filet section of a gas turbine blade, the detection head operable to move along the axial length of the filet section for detecting corrosion pitting;
   (b) at least one coil device located within the detection head and operable to induce a first magnetic field within an area of the filet in contact with the detection head;
   (c) a receiver device operable to detect a signal corresponding to a second magnetic field received from the area of the filet exposed to the first magnetic field, wherein the second magnetic field is generated by induced currents in the area by the first magnetic field; and
   (d) a signal processing device operable to process the detected signal for correlating a corresponding amplitude of the detected signal with the presence of corrosion pitting in the area,
   wherein the presence of corrosion pitting is determined without any casing disassembly of the gas turbine system, and the gas turbine blade comprises one of a plurality of first stage R1 rotary blades located behind a plurality of inlet guide; and
   further comprising a handle section coupled to the detection head, the handle section including a flexible portion operable to move the detection head into a measurement position by enabling contact between the detection head and the filet section of the one of a plurality of first stage R1 rotary blades based on manipulating the flexible portion and detection head between the plurality of inlet guide vanes.

12. The device according to claim 11, further comprising a video camera coupled to the handle section, the video camera located in proximity to the detection head and operable to assist an operator move the detection head into the measurement position.

13. A probe device for detecting corrosion in one or more blades of a gas turbine system, the device comprising:
   (a) a detection head having a shape that conforms to a surface geometry of a filet section of a gas turbine blade, the detection head operable to move along the axial length of the filet section for detecting corrosion pitting;
   (b) at least one coil device located within the detection head and operable to induce a first magnetic field within an area of the filet in contact with the detection head;
   (c) a receiver device operable to detect a signal corresponding to a second magnetic field received from the area of the filet exposed to the first magnetic field, wherein the second magnetic field is generated by induced currents in the area by the first magnetic field; and
   (d) a signal processing device operable to process the detected signal for correlating a corresponding amplitude of the detected signal with the presence of corrosion pitting in the area,
   wherein the presence of corrosion pitting is determined without any casing disassembly of the gas turbine system, and wherein the signal processing device comprises a digital signal processing (DSP) device comprising:
   (i) an analog-to-digital convertor operable to digitize the detected signal amplitude;
   (ii) a first storage region operable to store an amplitude corresponding to the detected signal with other stored detected signal amplitudes based on the amplitude corresponding to the detected signal and the other stored detected signal amplitudes corresponding to a detected corrosion pit;

(iii) a second storage region operable to store reference data associated with a plurality of pre-generated corrosion pitting areas created on a sample filet surface of a gas turbine blade; and (iv) a processor section operable to compare the amplitude corresponding to the detected signal with the stored reference data for determining the presence of corrosion pitting in the filet section.

14. The device according to claim 13, wherein the first storage region comprises time-stamp information that is added to both the amplitude corresponding to detected signal and the other stored detected signal amplitudes for calculating a time interval between the determination of corrosion pitting in the filet section.

15. The device according to claim 13, wherein the first storage region comprises drive signal information that is added to the stored detected signal amplitude and the other stored detected signal amplitudes for assessing the determination of corrosion pitting in the filet section.

16. A probe device for detecting corrosion in one or more blades of a gas turbine system, the device comprising:
  (a) a detection head having a shape that conforms to a surface geometry of a filet section of a gas turbine blade, the detection head operable to move along the filet section for detecting corrosion pitting;
  (b) at least one transducer device located within the detection head and operable to induce a first magnetic field within an area of the filet in contact with the detection head;
  (c) a receiver device operable to detect a signal corresponding to a second magnetic field received from the area of the filet exposed to the first magnetic field, wherein the second magnetic field is generated by induced currents in the area by the first magnetic field; and
  (d) a signal processing device operable to process the detected signal for correlating a corresponding amplitude of the detected signal with the presence of corrosion pitting in the area,
  wherein the presence of corrosion pitting is determined without any casing disassembly of the gas turbine system; and
  wherein the receiver device comprises:
  (i) a first and a second coil device operable to generate a first and a second received signal from the second magnetic field, respectively;
  (ii) a first and a second band-pass filter device respectively coupled to the first and the second coil device, wherein the first and the second band-pass filter device are operable to filter the first and the second received signal, respectively; and
  (iii) a differential amplifier device coupled to the first and the second band-pass filter device, wherein the differential amplifier is operable to differentially amplify the filtered first and the filtered second received signal and generate the detected signal.

17. A probe device for detecting corrosion in one or more blades of a gas turbine system, the device comprising:
  (a) a detection head having a shape that conforms to a surface geometry of a filet section of a gas turbine blade, the detection head operable to move along the filet section for detecting corrosion pitting;
  (b) a transceiver device located within the detection head and operable to induce a first magnetic field within an area of the filet in contact with the detection head and detect a signal corresponding to a second magnetic field received from the area of the filet exposed to the first magnetic field, wherein the second magnetic field is generated by induced currents in the area by the first magnetic field; and
  (c) a signal processing device operable to process the detected signal for correlating a corresponding amplitude of the detected signal with the presence of corrosion pitting in the area,
  wherein the presence of corrosion pitting is determined without any casing disassembly of the gas turbine system; and
  wherein the receiver comprises:
  (i) a second coil device;
  (ii) a third coil device; and
  (iii) a differential amplifier coupled to the second and the third coil device and operable to differentially amplify a second and a third signal received from the second and the third coil device, respectively, wherein the differential amplifier generates the detected signal.

18. The device according to claim 17, wherein the transceiver device comprises:
  (a) a transmitter operable to generate the first magnetic field; and
  (b) a receiver operable to receive the second magnetic field and generate the detected signal amplitude.

19. The device according to claim 17, wherein the transmitter comprises:
  (a) a first coil device; and
  (b) a coil driver operable to apply an electrical drive signal to the first coil device.

20. The device according to claim 17, wherein the second and the third coil each comprise:
  (a) a coil diameter of about 1.6-2.0 millimeters;
  (b) a cylindrical coil support;
  (c) a coil frequency range of about 50-900 KHz; and
  (d) a coil signal to noise ratio of about 5/1.

21. A method of detecting corrosion in one or more blades of a gas turbine system, the method comprising:
  (a) detecting corrosion pitting along the axial length of a filet section of a gas turbine blade by conforming the detecting to the surface geometry of the filet section;
  (b) inducing a first magnetic field within an area of the filet during the detecting of the corrosion;
  (c) detecting a signal corresponding to a second magnetic field received from the area of the filet exposed to the induced first magnetic field, wherein the second magnetic field is generated by induced currents in the area by the induced first magnetic field;
  (d) processing the detected signal by correlating a corresponding amplitude of the detected signal with the presence of corrosion pitting in the area;
  (e) imaging the gas turbine blade using an imaging device for facilitating the detecting of corrosion pitting; and
  (f) displaying the imaged gas turbine blade to user;
  wherein the presence of corrosion pitting is determined without any casing disassembly of the gas turbine system.

22. The method according to claim 21, wherein conforming the detecting to the surface geometry comprises using a probe head having a cylindrical shape that includes a radius that is substantially the same as or less than a radius of curvature associated with the filet section.

23. A probe device for detecting corrosion in one or more blades of a gas turbine system, the device comprising:

(a) a detection head having a shape that conforms to a surface geometry of a filet section of a gas turbine blade, the detection head operable to move along the axial length of the filet section for detecting corrosion pitting;

(b) at least one coil device located within the detection head and operable to induce a first magnetic field within an area of the filet in contact with the detection head;

(c) a receiver device operable to detect a signal corresponding to a second magnetic field received from the area of the filet exposed to the first magnetic field, wherein the second magnetic field is generated by induced currents in the area by the first magnetic field; and (d) a signal processing device operable to process the detected signal for correlating a corresponding amplitude of the detected signal with the presence of corrosion pitting in the area, wherein the presence of corrosion pitting is determined without any casing disassembly of the gas turbine system;

wherein the at least one coil device comprises a plurality of coil devices located within the detection head and operable to each induce the first magnetic field within an area of the filet in contact with the detection head;

wherein said detected signal comprises a plurality of signals corresponding to said second magnetic field; and wherein said signal processing device is operable to process the plurality of detected signals for correlating corresponding amplitudes of the detected signals with the presence of corrosion pitting in the area, wherein each of the processed plurality of detected signals corresponds to a signal channel associated with a respective one of the plurality of coil devices, thereby providing for multi-channel detection of corrosion pitting.

24. A corrosion pitting detection unit comprising a plurality of probe devices, wherein each probe device includes:

(a) a detection head having a shape that conforms to a surface geometry of a filet section of a gas turbine blade, the detection head operable to move along the axial length of the filet section for detecting corrosion pitting;

(b) at least one coil device located within the detection head and operable to induce a first magnetic field within an area of the filet in contact with the detection head;

(c) a receiver device operable to detect a signal corresponding to a second magnetic field received from the area of the filet exposed to the first magnetic field, wherein the second magnetic field is generated by induced currents in the area by the first magnetic field; and (d) a signal processing device operable to process the detected signal for correlating a corresponding amplitude of the detected signal with the presence of corrosion pitting in the area, wherein the presence of corrosion pitting is determined without any casing disassembly of the gas turbine system, and wherein the results of the detected signal processed by each signal processing device of the plurality of probe devices is output on a corresponding channel; and wherein each receiver device comprises:

(i) a first and a second coil device operable to generate a first and a second received signal from the second magnetic field, respectively;

(ii) a first and a second band-pass filter device respectively coupled to the first and the second coil device, wherein the first and the second band-pass filter device are operable to filter the first and the second received signal, respectively; and (iii) a differential amplifier device coupled to the first and the second band-pass filter device, wherein the differential amplifier is operable to differentially amplify the filtered first and the filtered second received signal and generate the detected signal.

\* \* \* \* \*